Jan. 30, 1962 E. S. BOERNER Plant Pat. 2,127
CHRYSANTHEMUM PLANT
Filed March 17, 1961
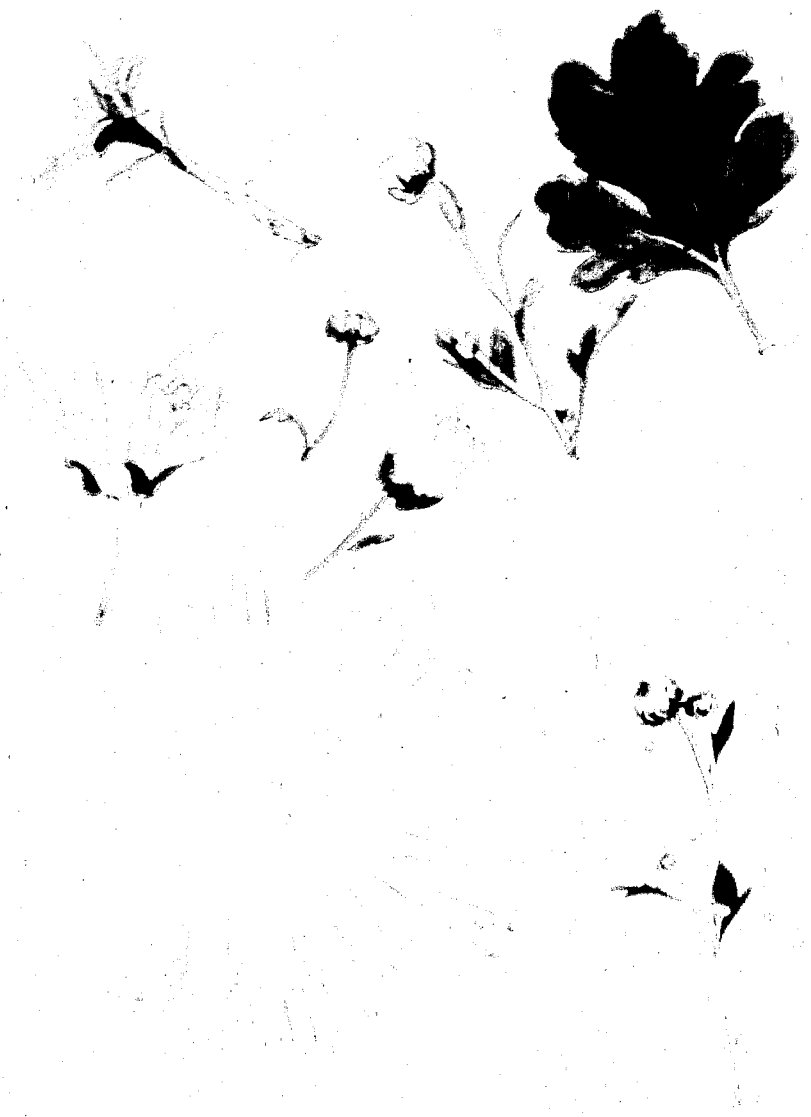
Inventor.
E. S. Boerner
By: Robb & Robb
Attorneys.

United States Patent Office

Plant Pat. 2,127
Patented Jan. 30, 1962

2,127
CHRYSANTHEMUM PLANT

Eugene S. Boerner, Newark, N.Y., assignor to Jackson & Perkins Company, Newark, N.Y., a corporation of New York Filed Mar. 17, 1961, Ser. No. 96,629
1 Claim. (Cl. 47—60)

The present invention relates to a new and distinct variety of chrysanthemum plant of the decorative class, which was orginated by me by crossing an unnamed and unpatented seedling derived from a cross of "Meadowlark" (Plant Patent No. 1,305) × "Thrush" (Plant Patent No. 1,168) with the variety known as "Kingbird" (Plant Patent No. 1,306).

The primary objective of this breeding was to produce a new chrysanthemum variety which combines the earliness of the unnamed parent seedling with the color and bloom size of the parent "Kingbird." This objective was fully achieved, along with other desirable improvements, as evidenced by the following characteristics which are outstanding in the new variety and which distinguish it from its parents, as well as from all other varieties of which I am aware:

(1) Very large foliage size;

(2) A distinctive habit of the flower petals in curling quill-fashion at the finish;

(3) A very sweet flower fragrance; and (4) A distinctive general color tonality of the flowers corresponding to Thulite Pink, lightly overcast with Spinel Pink, and with the lower half of the petals lightly overcast with Ivory Yellow.

Asexual reproduction of my new variety by both top cuttings and underground runners, as performed at Newark, New York, shows that the foregoing characteristics and distinctions come true to form and are established and transmitted through succeeding propagations.

The accompanying drawing shows typical specimens of the vegetative growth and flowers of my new chrysanthemum variety in different stages of development and as depicted in color as nearly true as it is reasonably possible to make the same in a color illustration of this character, as well as a typical specimen plant which is depicted in black-and-white for the purpose of illustrating the form and habit of growth of the plant.

The following is a detailed description of the new variety, with color terminology in accordance with Ridgway's Color Standards and Nomenclature, as based upon observations of specimens grown outdoors at Newark, New York, in the early morning during the latter part of the month of October:

Parentage: Seedling.
- Seed parent.—A unnamed seedling of "Meadowlark" × "Thrush."
- Pollen parent.—"Kingbird."

Classification: Decorative.
Growth: Very free.

Cold resistance: Very winter hardy in northern New York State.
Blooming period: In the Newark, New York, climatic area, blooming begins about the end of September and continues until frost.

*Flower*

Bud:
- Color.—When sepals first divide—Indian Lake, Plate 26. When petals begin to unfurl—Spinel Red, Plate 26, lightly overcast with Spinel Pink, Plate 26. When half-blown: inside of petals—Spinel Red, Plate 26; outside of petals—Amaranth Purple, Plate 12, lightly overcast with Rose Color, Plate 12.
- Peduncle.—Color—Light Cress Green, Plate 31. Strength—strong.

Bloom:
- Size.—6 inches.
- Stem.—Strong.
- Form.—Decorative.
- Petalage.—Double.
- Color.—Center of flower—Thulite Pink, Plate 26, with lower half of petals lightly overcast with Ivory Yellow, Plate 30. Outer petals—Rhodonite Pink, Plate 38, lightly overcast with Spinel Pink, Plate 26 on the outer edge of the petals. Base of petals—Baryta Yellow, Plate 4. Inside of petals —Thulite Pink, Plate 26, lightly overcast with Spinel Pink, Plate 26, and with lower half of petals lightly overcast with Ivory Yellow, Plate 30. Reverse of petals—Thulite Pink, Plate 26, lightly overcast with Cameo Pink, Plate 26.
- Petals.—Texture—thick. Form—curl quill-fashion at finish.
- Fragrance.—Very sweet.

*Plant*

Form: Upright; branching.
Growth: Very free.
Foliage:
- Size.—Very large.
- Quantity.—Heavy.
- Color.—Upper side—Varley's Green, Plate 18. Reverse side—Light Cress Green, Plate 31.
- Texture.—Leathery.

I claim:

A new and distinct variety of chrysanthemum plant of the decorative class, substantially as herein shown and described, characterized particularly as to novelty by the unique combination of a very large foliage size, a habit of the flower petals in curling quill-fashion at the finish, a very sweet flower fragrance, and a distinctive general color tonality of the flowers corresponding to Thulite Pink, lightly overcast with Spinel Pink, and with the lower half of the petals lightly overcast with Ivory Yellow.

No references cited.